(12) United States Patent
Cowan et al.

(10) Patent No.: US 12,213,947 B2
(45) Date of Patent: Feb. 4, 2025

(54) LOCKABLE ADAPTER ASSEMBLY

(71) Applicant: GBUK Group Limited, Selby (GB)

(72) Inventors: Joseph Cowan, Selby (GB); Ross Allsopp, Selby (GB); Nicholas Scard, Selby (GB)

(73) Assignee: GBUK Group Limited, Selby (GB)

( * ) Notice: Subject to any disclaimer, the term of this patent is extended or adjusted under 35 U.S.C. 154(b) by 676 days.

(21) Appl. No.: 17/147,041

(22) Filed: Jan. 12, 2021

(65) Prior Publication Data

US 2021/0212902 A1  Jul. 15, 2021

(30) Foreign Application Priority Data

Jan. 13, 2020 (GB) ..................................... 2000443

(51) Int. Cl.
*A61J 15/00* (2006.01)
*A61M 39/10* (2006.01)
*A61M 39/20* (2006.01)

(52) U.S. Cl.
CPC ....... *A61J 15/0026* (2013.01); *A61J 15/0011* (2013.01); *A61M 39/1011* (2013.01);
(Continued)

(58) Field of Classification Search
CPC .... A61J 15/0026; A61J 15/0011; A61J 15/00; A61J 7/0053; A61M 39/10;
(Continued)

(56) References Cited

U.S. PATENT DOCUMENTS

2003/0191445 A1  10/2003 Wallen et al.
2008/0185056 A1  8/2008 Diodati et al.
(Continued)

FOREIGN PATENT DOCUMENTS

JP        2012066866 A    4/2012
WO   WO-2018086911 A1   5/2018

OTHER PUBLICATIONS

GB Search Report for Application No. GB2000443.8 dated Jul. 8, 2020.
(Continued)

*Primary Examiner* — Kevin C Sirmons
*Assistant Examiner* — Alexandra Lalonde
(74) *Attorney, Agent, or Firm* — Harness, Dickey & Pierce, PLC

(57) ABSTRACT

An enteral adapter assembly for connecting an enteral fluid source to an enteral feed tube, the enteral adapter assembly comprising: an adapter including: a proximal end comprising a first connection portion for attaching to a fluid outlet provided on the enteral fluid source, and a distal end comprising a first threaded connection portion for screwing to an end of the enteral feed tube. A fluid conduit extends between the proximal and distal ends. The assembly comprises a removable cap having a second threaded connection portion configured for screwing the cap onto the first threaded connection portion, wherein the proximal end of the adapter comprises a locking member configured to irreversibly mate with a corresponding feature provided on
(Continued)

the fluid outlet as the adapter is attached to the outlet to prevent removal of the adapter from the outlet when the cap is unscrewed from the distal end of the adapter.

16 Claims, 18 Drawing Sheets

(52) U.S. Cl.
CPC ..... *A61M 39/20* (2013.01); *A61M 2039/1033* (2013.01); *A61M 2039/1077* (2013.01); *A61M 2202/0482* (2013.01)

(58) Field of Classification Search
CPC .............. A61M 39/1011; A61M 39/20; A61M 39/1055; A61M 2039/1033; A61M 2039/1038; A61M 2039/1077; A61M 2039/1094; A61M 2202/0482; A61M 39/165; A61M 5/5086; A61M 39/00; A61M 39/08; A61M 39/12; A61M 2039/1027; A61M 2039/1044; A61M 2039/1066; A61M 2039/1083; A61M 2039/1088; A61M 2005/3104; A61M 2005/312
See application file for complete search history.

(56) References Cited

U.S. PATENT DOCUMENTS

| | | |
|---|---|---|
| 2012/0029481 A1 | 2/2012 | Pech et al. |
| 2012/0316537 A1 | 12/2012 | Meyer et al. |
| 2014/0276651 A1* | 9/2014 | Schultz ............... A61M 39/165 53/425 |
| 2014/0339811 A1* | 11/2014 | Wong .................... A61J 1/2096 29/525.02 |
| 2016/0361235 A1* | 12/2016 | Swisher ................ A61M 39/12 |
| 2017/0014310 A1* | 1/2017 | Hyun ................. A61J 15/0026 |
| 2017/0014616 A1* | 1/2017 | Davis .................... A61M 39/10 |
| 2017/0173321 A1* | 6/2017 | Davis ................. A61M 5/3134 |
| 2017/0203086 A1 | 7/2017 | Davis |
| 2017/0312181 A1* | 11/2017 | Davis .................... A61M 39/10 |
| 2018/0078753 A1 | 3/2018 | Jones |
| 2018/0126094 A1* | 5/2018 | Reid ................... A61M 5/1458 |

OTHER PUBLICATIONS

Extended European Search Report regarding EP 21150418.8, dated Jun. 11, 2021.

* cited by examiner

LOCKABLE ADAPTER ASSEMBLY

CROSS-REFERENCE TO RELATED APPLICATIONS

This application claims priority to British Patent Application No. GB 2000443.8, filed Jan. 13, 2020. The entire disclosure of the above application is incorporated herein by reference.

FIELD OF THE INVENTION

This invention relates to a lockable adapter assembly for use in connecting a fluid source to a fluid conduit, and more particularly a lockable adapter assembly for use in connecting an enteral fluid source to an enteral fluid conduit. The invention also relates to kits including the lockable adapter assembly, and method of connecting a fluid source to a fluid conduit using the adapter.

BACKGROUND OF THE INVENTION

Fluid delivery systems, such as feeding tubes, are used to deliver nutrients and medicine to patients. The state of being fed by a feeding tube is commonly known in the art as enteral feeding.

As an example, in a neo-natal unit, infants are often fed enterally. A tube is inserted in the mouth or nasal opening of the infant and through the esophagus for delivery of the fluid into the gastrointestinal system. In this example, breast milk or formula are delivered by a syringe or via the port of an enteral feeding bag into an enteral delivery system, such as an enteral tube, for delivery into the infant's stomach. However, enteral feeding systems can also be for pediatric or adult use.

Tubing and catheter misconnection errors are an important and potentially deadly problem in healthcare facilities. One type of tube and catheter misconnection error involves enteral feeding tubes and intravenous catheters. Whilst enteral feeding tubes, such as nasogastric feeding tubes, are used to administer liquid nutritional solutions and medications into a patient's gastrointestinal system, intravenous catheters are used to administer liquid nutritional solutions and medications directly into a patient's vascular system. Serious injury, and even death, can occur when substances designed for enteral administration are administered intravenously.

The widespread use of luer connectors for medical tubing, catheters and syringes has contributed to the risk of error as they enable functionally dissimilar tubes or catheters to be connected. This has led to the establishment of International Standard: ISO 80369-3 for small bore connectors for liquids and gases. The design requirements make it difficult, if not impossible, for unrelated delivery systems to be connected. ISO 80369-3 connectors for enteral devices are commonly referred to as ENFit connectors.

The feeding of a liquid enteral nutritional solution from a container such as from a feeding bottle or bag requires a detachable connection to be made between the container's fluid outlet port and an end of the enteral feeding tube. In order to adhere to the ISO standard, this detachable connection is via a complementary ENFit connection which is based on a complementary connection between a male threaded ENFit connector and a female threaded ENFit connector.

The threaded fluid outlet port of many designs of feeding bottle or bag is incompatible with the ENFit connector provided on the end of an enteral feeding tube. In such circumstances, an ENFit bottle adapter is threaded onto the fluid outlet port in order to convert the fluid outlet port into a compatible ENFit connector.

During pauses in enteral feeding, it is necessary for the fluid outlet port to be temporarily closed to prevent any leakage of the nutritional solution. Closure is often achieved via the use of a removable threaded cap. The co-existence of two threaded connections at the fluid outlet port (i.e., a first threaded connection between the adapter and the fluid outlet port, and a second threaded connection between cap and the adapter) may result in the adapter being partially unscrewed from the fluid outlet port when the cap is unscrewed. Such inadvertent unscrewing of the adapter can result in the fluid-tight seal between the adapter and the port being broken, and subsequent leakage of the enteral feeding solution. broken. Not only is this wasteful, from a cost perspective, but any spilt enteral fluid can have significant hygiene and safety implications. For example, bacteria may colonise any spilt enteral fluid, and then enter the enteral feeding system. Additionally, in the case of the administration of a medicine, the patient may receive an underdose.

A need therefore exists for an adapter than is permanently locked on the fluid outlet and which cannot be inadvertently loosened.

SUMMARY OF THE INVENTION

According to a first aspect of the invention there is provided an enteral adapter assembly for connecting an enteral fluid source to an enteral feed tube, the assembly comprising:
  an adapter including:
    a proximal end comprising a first connection portion for attaching to a fluid outlet provided on the enteral fluid source, and
    a distal end comprising a first threaded connection portion for screwing to an end of an enteral feed tube, and
    a fluid conduit extending between the proximal and distal ends,
  the assembly further comprising:
    a removable cap having a second threaded connection portion configured for screwing the cap onto the first threaded connection portion,
  wherein the proximal end of the adapter further comprises a locking member configured to irreversibly mate with a corresponding feature provided on the fluid outlet of the enteral fluid source as the adapter is attached to the outlet to prevent removal of the adapter from the outlet when the cap is unscrewed from the distal end of the adapter.

In some constructions, the first threaded connection portion provided at the distal end of the adapter is an ENFit connector. For example, the first threaded connection portion is a female ENFit connector which is configured to mate with a corresponding male ENFit connector provided at an end of an enteral feed tube. In other constructions, the first threaded connection portion is a male ENFit connector which is configured to mate with a corresponding female ENFit connector provided at an end of an enteral feed tube.

In the constructions in which the first threaded connection portion provided at the distal end of the adapter is a female ENFit connector, the second threaded connection portion provided on the removable cap is a corresponding male ENFit connector. In the constructions in which the first threaded connection portion provided at the distal end of the adapter is a male ENFit connector, the second threaded connection portion provided on the removable cap is a corresponding female ENFit connector.

In some constructions, the mechanism of attaching the adapter to the fluid outlet on the enteral fluid source involves screwing the adapter onto the outlet. Accordingly, the first connection portion provided at the proximal end of the adapter may comprise a third threaded connection portion, configured to form a screw connection with the fluid outlet.

The third threaded portion may be a female or a male screw thread provided on an internal surface of the proximal end of the adapter.

The enteral fluid source may be an enteral feed bag or pouch. The fluid outlet may be a nozzle or a spout provided on the enteral feed bag or pouch.

During the attachment of the enteral adapter assembly to the fluid outlet the locking member provided on the proximal end of the adapter irreversibly mates with a corresponding feature provided on the fluid outlet. In some constructions, the corresponding feature provided on the outlet of the enteral feed source is a part of an anti-tamper mechanism. An example of such a mechanism is a tamper-evident ring. Such an anti-tamper mechanism interacts with a cap which is attached to the fluid outlet of the enteral feed source once the enteral feed source (e.g., bag or pouch) has been filled with the enteral fluid. This cap seals the outlet of the enteral feed source. This cap may be referred to as the "primary cap".

In advance of connecting the enteral feed source to the enteral feed tube, the user confirms that the enteral feeding source has not been previously opened (e.g., that the contents have not been tampered with, that enteral fluid has not been removed, or that there has been a breach in the sterility of the enteral fluid) by assessing whether the connection between the anti-tamper mechanism on the fluid outlet and the cap is intact. The primary cap is then removed and discarded, and the user can attach the adapter assembly according to the first aspect of the invention to the fluid outlet. The cap forming parted of the inventive adapter assembly ass herein may be referred to as the "secondary cap". This secondary cap is used for the temporary closure of adapter when the enteral feeding is paused, and the adapter is disconnected from the enteral feed tube.

The locking member may comprise a deflectable element that is configured to deflect during the attachment of the adapter to the fluid outlet, and thereby irreversibly and permanently mate the adapter with the fluid outlet.

The fluid outlet may include a single corresponding feature which is configured to irreversibly mate with the single respective locking member (e.g. deflectable element).

The locking member may comprise a plurality of deflectable elements that are spaced apart about the proximal end of the adapter. For example, the plurality of deflectable elements may be circumferentially arranged about the proximal end of the adapter. In some constructions, a first deflectable element and a second deflectable element may be positioned diametrically opposite each other at the proximal end of the adapter.

The fluid outlet may comprise a plurality of corresponding features, with each feature being configured to mate with a respective one of a plurality of deflectable elements.

In some constructions of the adapter assembly, the or each of the deflectable elements has a most proximally placed contact face, which as described below is the part of the adapter that initially interacts with the corresponding feature or features on the fluid outlet to cause the permanent locking of the adapter onto the fluid outlet.

The distance that the or each of the deflectable elements is deflected during attachment of the adapter to the fluid outlet is preferably sufficient to allow the adapter to positioned on the fluid outlet to form a fluid tight seal.

The reversion of the deflectable element to its original position once the adapter has been seated on the fluid outlet results in the permanently locking of the adapter on the fluid outlet, and prevents the inadvertent removal (e.g. by unscrewing) of the adapter, when the secondary cap is removed (e.g. unscrewed).

The corresponding feature or features on the fluid outlet may be a protrusion. For example, a single protrusion or a plurality of spaced apart protrusions may extend in a distal direction.

In a particular construction, a tamper-evident ring provided on the fluid outlet may comprise a collar from which a single protrusion or a plurality of spaced apart protrusions may extend in a distally direction.

When the adapter is screwed onto the fluid outlet contact between the most proximally placed contact surface on the deflectable element and a contact point on the corresponding feature causes the or each deflectable element to be deflected distally.

In some constructions, the most proximally placed contact face may comprise or consist of a ramped surface. As the adapter is screwed onto the fluid outlet, the contact point on the or each corresponding feature rides along the ramped surface of the or each deflectable element. The contact point continues to ride along the ramped surface until the downward force applied by the corresponding feature via the contact point is sufficient to cause deflection of the deflectable element.

The or each deflectable element may comprise a locking face which is brought into a locking engagement with a corresponding locking face on the corresponding feature provided on the fluid outlet, as the deflectable element is deflected during attachment of the adapter onto the fluid outlet. In some constructions, the locking face may be positioned substantially perpendicular to a longitudinal axis extending between the proximal end and the distal end of the adapter. In some other constructions, the locking face may be positioned substantially parallel to a longitudinal axis extending between the proximal end and the distal end of the adapter.

The or each of the deflectable elements may be a deflectable arm. The or each of the deflectable arms may extend at an angle to the longitudinal axis X of the adapter.

In some other constructions, the or each of the deflectable arms may extend substantially parallel to the longitudinal axis X of the adapter. The pair of deflectable arms may define a juxtaposable jaw.

A hinge may be provided at a point along the length of the or each arm to enable deflection of the or each arm in a distal direction. The hinge may be provided by a localised thinned area of material.

In some constructions, the cap is tethered to the adapter.

According to a second aspect of the invention, there is provided a kit comprising an enteral adapter assembly as described according to the first aspect of the invention and an enteral feed tube.

According to a third aspect of the invention, there is provided a kit comprising an enteral adapter assembly as described according to the first aspect of the invention and an enteral fluid source.

According to a fourth aspect of the invention, there is provided a method of connecting an enteral fluid source to an enteral feed tube comprising the steps of:

(a) providing an enteral adapter assembly comprising:
   an adapter including:
      a proximal end comprising a first connection portion for attaching to a fluid outlet provided on the enteral fluid source, and
      a distal end comprising a first threaded connection portion for screwing to an end of an enteral feed tube, and
      a fluid conduit extending between the proximal and distal ends,
   the assembly further comprising:
      a removable cap having a second threaded connection portion configured for screwing the cap onto the first threaded connection portion,
   wherein the proximal end of the adapter further comprises a locking member configured to irreversibly mate with a corresponding feature provided on the fluid outlet of the enteral feed source as the adapter is attached to the outlet to prevent removal of the adapter from the outlet when the cap is unscrewed from the distal end of the adapter,
(b) attaching the proximal end of the adapter to the fluid outlet, and
(c) attaching the distal end of the adapter to the enteral feed tube.

According to a fifth aspect of the invention there is provided an enteral adapter assembly for connecting an enteral fluid source to an enteral feed tube, the assembly comprising:
   a fluid outlet for connection with an enteral fluid source,
   an adapter including:
      a proximal end comprising a first connection portion for attaching to the outlet provided on the enteral fluid source, and
      a distal end comprising a first threaded connection portion for screwing to an end of an enteral feed tube, and
      a fluid conduit extending between the proximal and distal ends,
   the assembly further comprising:
      a removable cap having a second threaded connection portion configured for screwing the cap onto the first threaded connection portion,
   wherein the proximal end of the adapter further comprises a locking member configured to irreversibly mate with a corresponding feature provided on the outlet of the enteral feed source as the adapter is attached to the outlet to prevent removal of the adapter from the outlet when the cap is unscrewed from the distal end of the body.

Whilst the first aspect of the invention is directed to an adapter assembly for use in connecting an enteral fluid source to an enteral feed tube, it is envisaged that the adapter may be used in other medical or non-medical applications in which an adapter is required as an intermediate element to form the connection between the fluid source and the fluid conduit, and in which a user wants to be able to repeatedly unscrew a cap from the distal end of the adapter without the adapter being inadvertently unattached, (e.g., unscrewed) from the fluid outlet on the fluid source. For example, during the administration of intravenous or parenteral fluids.

Therefore, according to a sixth aspect of the invention there is provided an adapter assembly for connecting a fluid source to a fluid conduit, the assembly comprising:
   a fluid outlet for connection with a fluid source,
   an adapter including:
      a proximal end comprising a first connection portion for attaching to the outlet provided on the fluid source, and
      a distal end comprising a first threaded connection portion for screwing to an end of a fluid conduit, and
      a passage for fluid flow extending between the proximal and distal ends,
   the assembly further comprising:
      a removable cap having a second threaded connection portion configured for screwing the cap onto the first threaded connection portion,
   wherein the proximal end of the adapter further comprises a locking member configured to irreversibly mate with a corresponding feature provided on the outlet of the fluid source as the adapter is attached to the outlet to prevent removal of the adapter from the outlet when the cap is unscrewed from the distal end of the adapter.

BRIEF DESCRIPTION OF THE DRAWINGS

The invention will now be described, by way of example only, with reference to the following drawings, in which.

DETAILED DESCRIPTION OF THE DRAWINGS

First Exemplary Construction of the Enteral Adapter Assembly

With reference now to the drawings, FIGS. 1A-G show a first construction of an enteral adapter assembly for connecting an enteral fluid source (e.g., an enteral feed bag) to an enteral feed tube. The adapter assembly 10 includes an adapter 20 and a removable cap 30. The cap 30 is shown as being tethered to the adapter. This is advantageous as it prevents the user misplacing the cap.

Figure 1A:
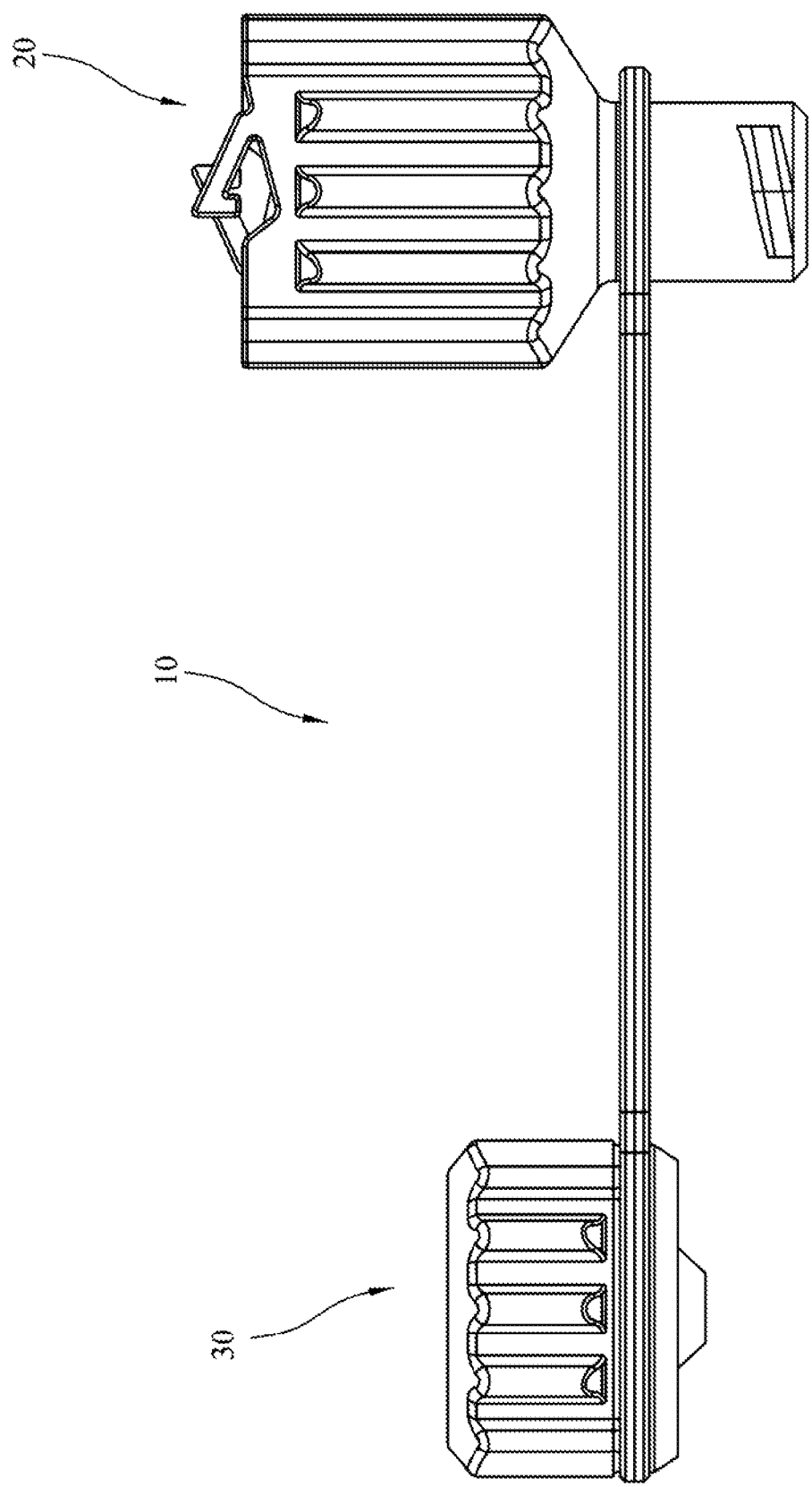
FIG. 1A is a perspective view a first construction of an enteral adapter assembly according to the invention showing the cap tethered to the adapter.
Figure 1B:
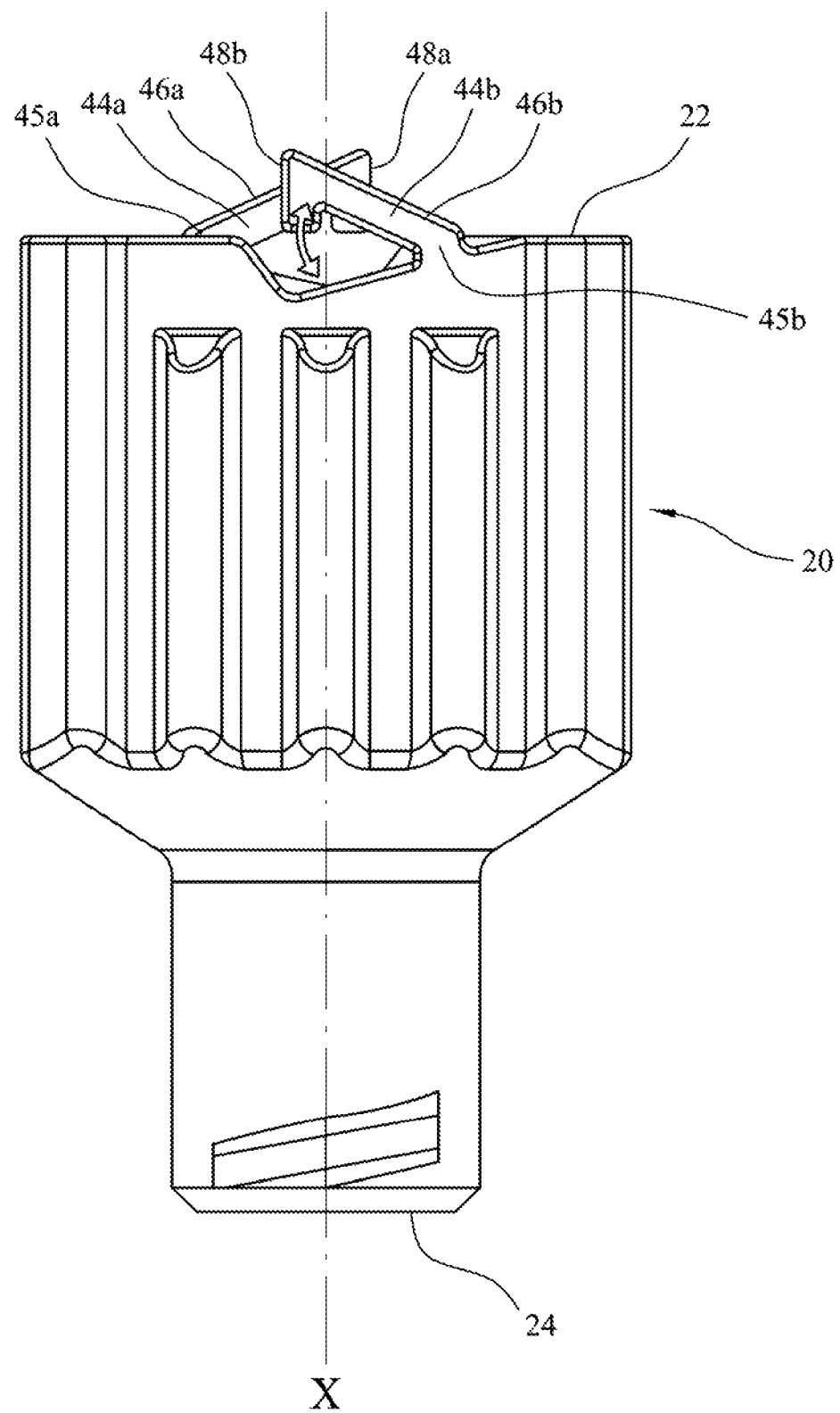
FIG. 1B is a front view of the adapter shown in FIG. 1A.

Turning to FIG. 1B, there is shown a front view of the adapter 20. The adapter has a proximal end 22 and a distal end 24, and a fluid conduit 26 extending therebetween. A longitudinal axis "X" extends lengthwise along the fluid conduit between the proximal end and the distal end of the adapter.

Figure 1C:
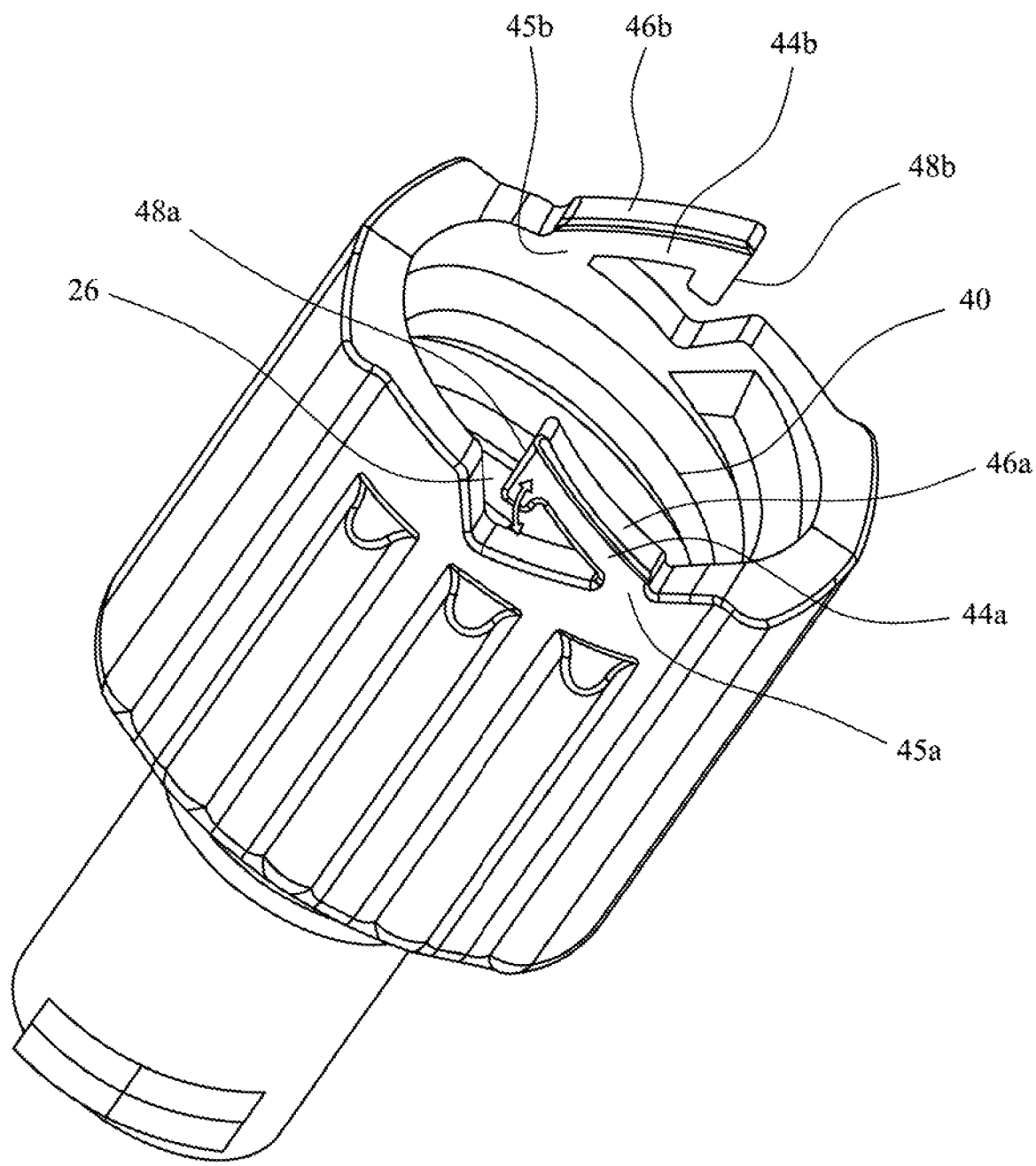
FIG. 1C is an isometric view of the adapter shown in FIG. 1B.
Figure 1D:
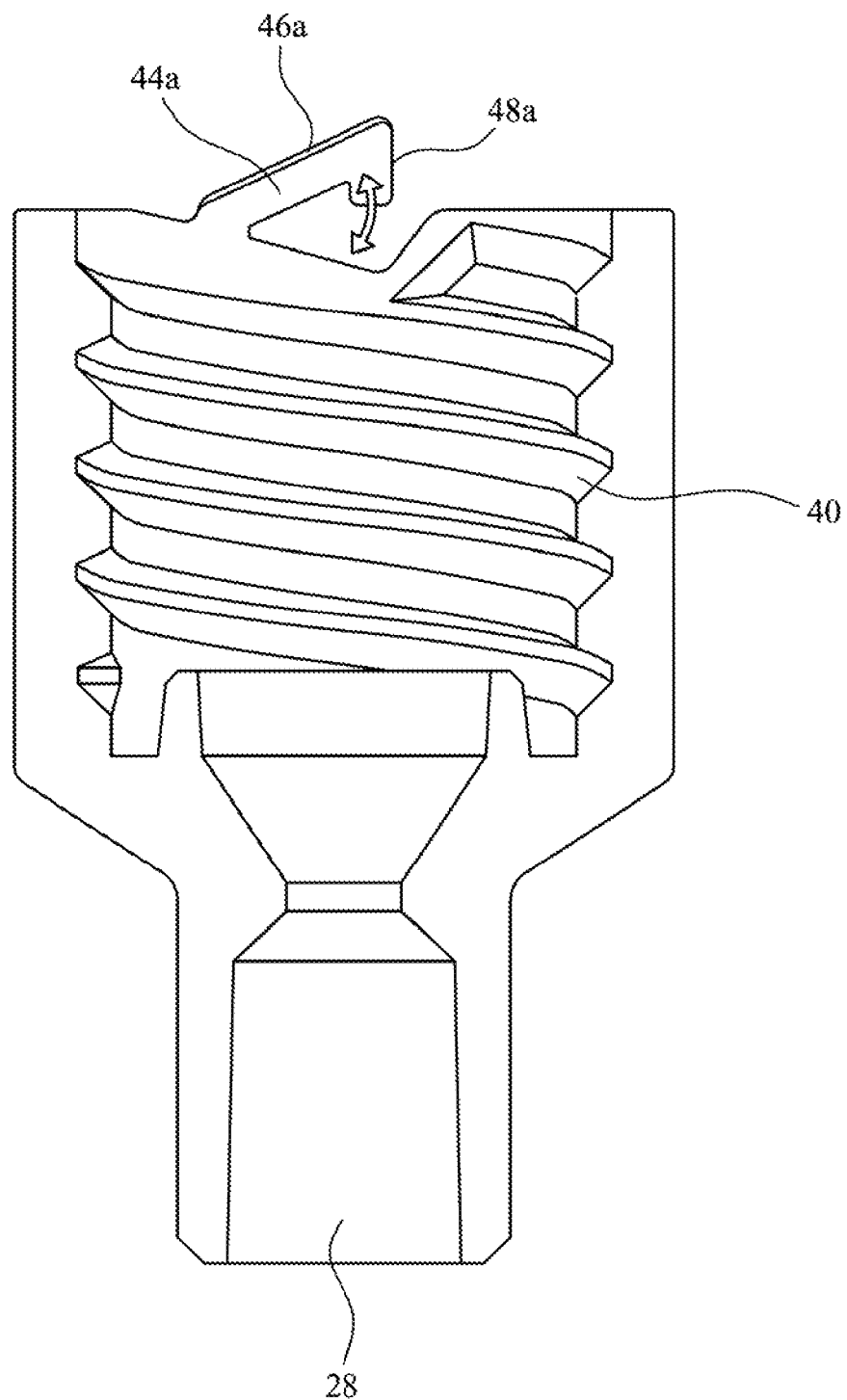
FIG. 1D is a cross-sectional view of the adapter assembly shown in FIG. 1B.
Figure 1E:
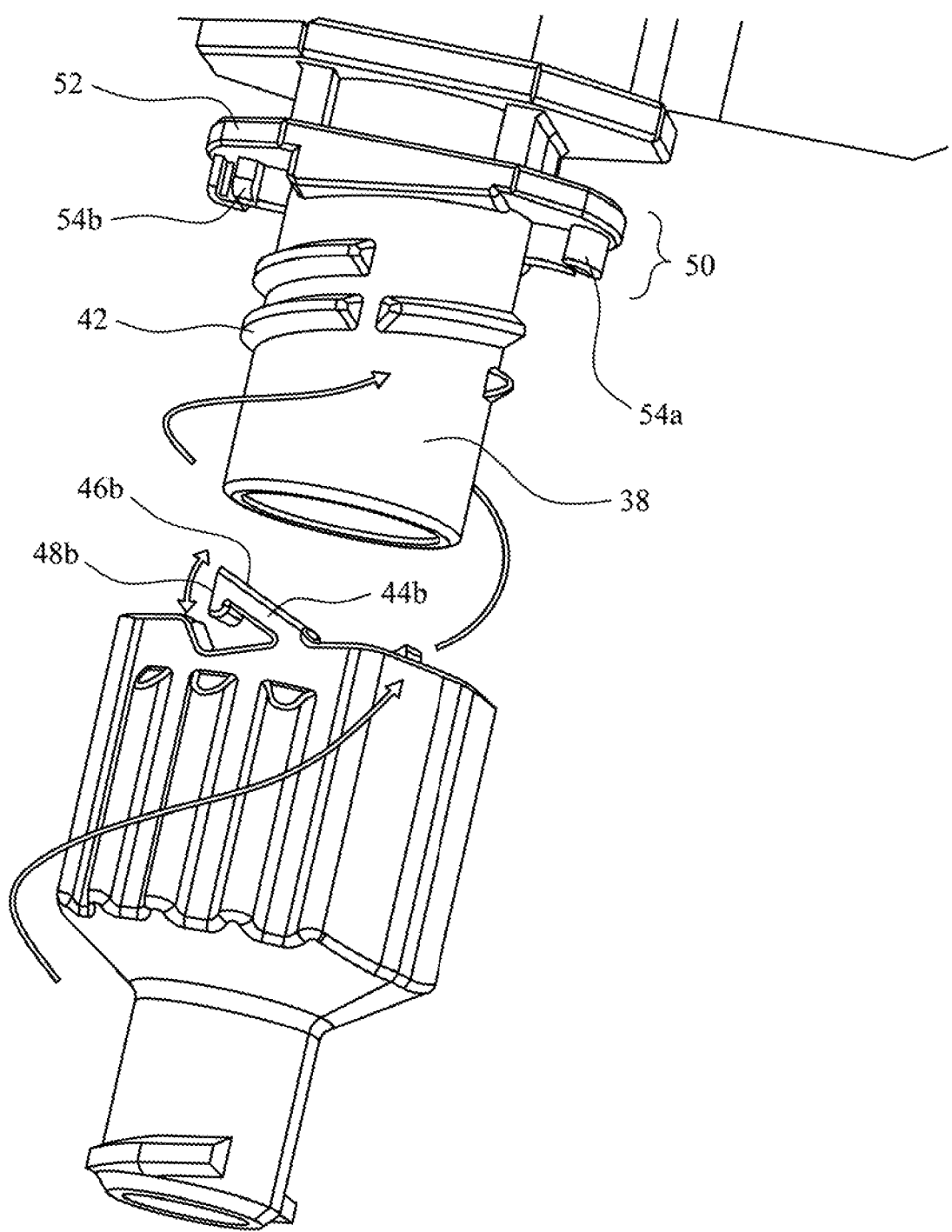
FIG. 1E is a perspective view of the adapter assembly of FIG. 1B before it has engaged with the fluid outlet on the fluid source.
Figure 1F:
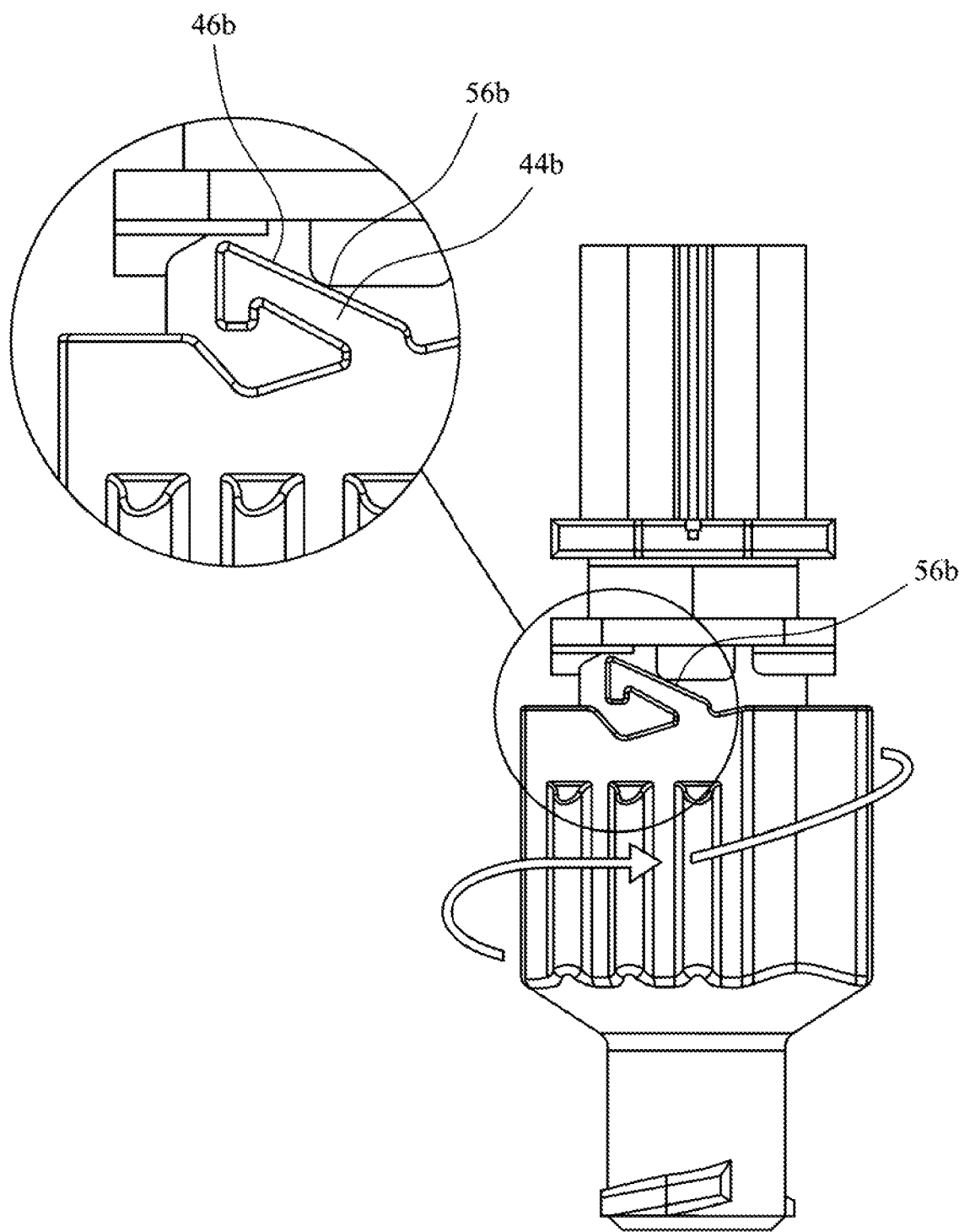
FIG. 1F is a perspective view of the adapter assembly of FIG. 1B in partial engagement with the fluid outlet on the fluid source.
Figure 1G:
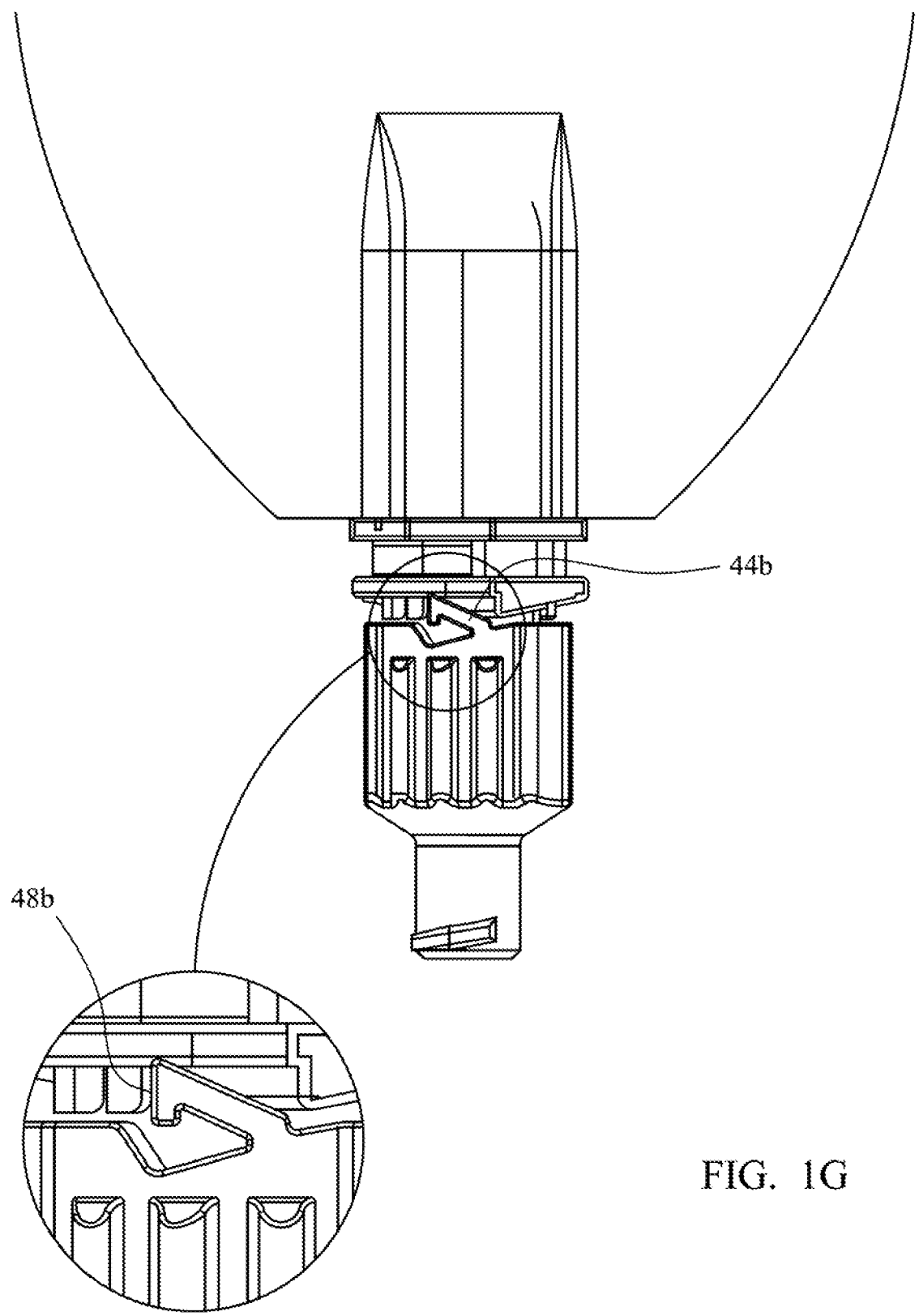
FIG. 1G is a perspective view of the adapter assembly of FIG. 1B in full engagement with the fluid outlet on the fluid source.
Figure 1H:
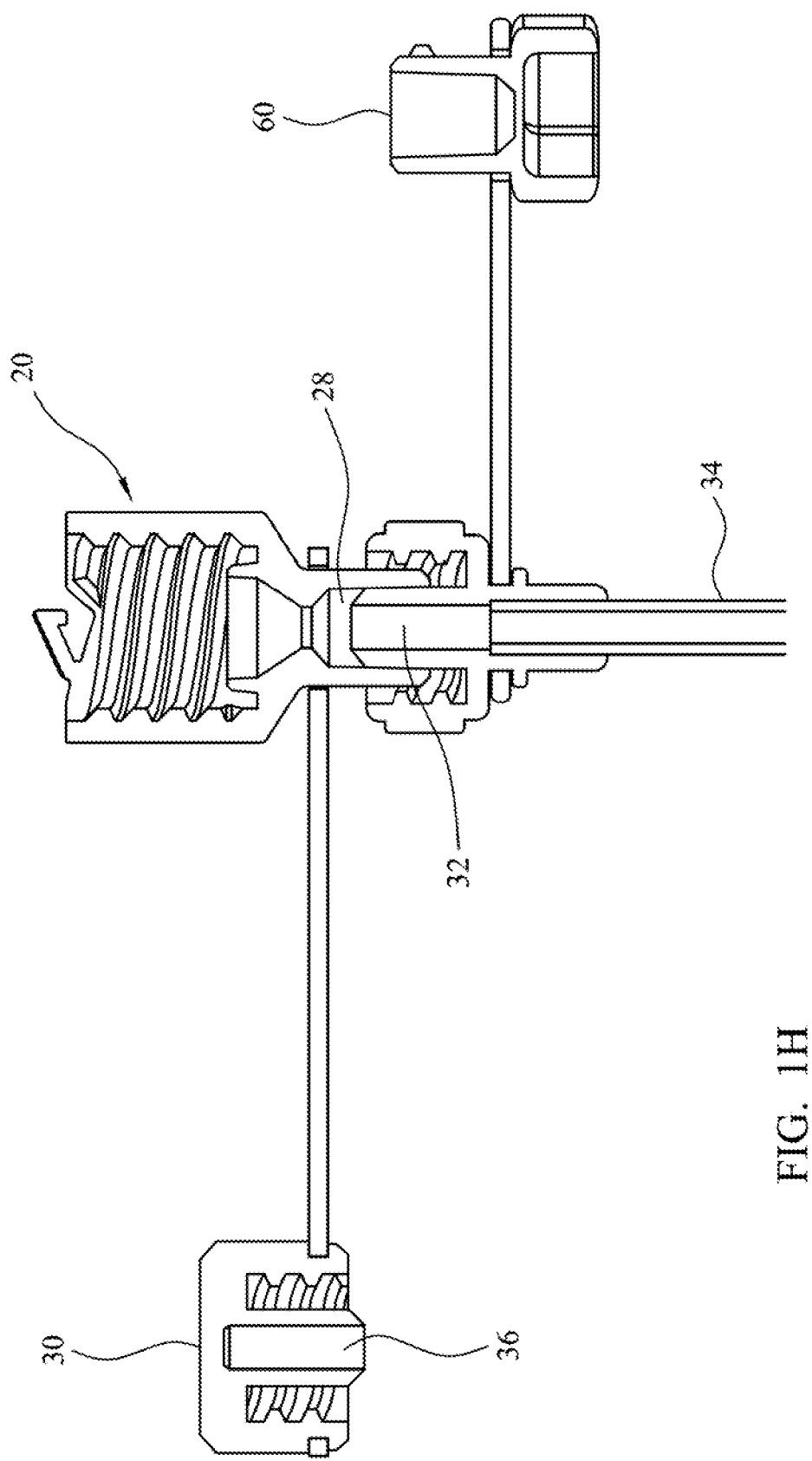
FIG. 1H is a perspective view of the adapter of FIG. 1B connected to an enteral fluid source and an enteral feed tube.

The distal end 24 of the adapter has a first threaded connection portion for removably screwing the adapter onto or into an end of an enteral feed tube. As shown in FIGS. 1D and 1G, the first threaded connection portion of adapter 10 is a female ENFit connector 28. This connector is configured to mate with a male ENFit connector 32 provided at the end of the enteral feed tube 34. A tethered cap 60 is provided on the enteral feeding tube itself and is used to cap off the tube in the same was as cap 30 caps off the adapter.

As also shown in FIG. 1G, the removable cap 30 includes a second threaded connection portion, here shown in the form of a male ENFit connector 36, configured to mate with the female ENFit connector 28 at the distal end of the adapter. This enables the cap to be removably screwed onto the adapter, when the adapter has been disconnected from the enteral feed tube.

The proximal end 22 of the adapter has a first connection portion for attaching the adapter to a fluid outlet, shown in the form of a nozzle 38 provided on the enteral fluid source. As shown in FIGS. 1C and 1D, in adapter 10 the first connection portion includes a third threaded connection portion in the form of a female screw thread 40 provided on a wall defining the fluid conduit 26. Screw thread 40 is configured to be screwed onto a corresponding male screw thread 42 provided on an external wall of the fluid outlet 38.

Adapter 10 includes a pair of diametrically opposed locking members in the form of deflectable arms 44a, 44b extending from the proximal end of the adapter. Each arm has a so called "hook-like" or "latch-like" design. Each deflectable arm is configured to deflect during attachment of the adapter to the nozzle, to reversibly mate each deflectable arm with a respective corresponding feature on the nozzle.

Each deflectable arm 44a, 44b extends at an angle from the proximal end of the adapter to the longitudinal axis X. The angle is at least 10°. The angle may be at least 20°, at least 30°, at least 35°, at least 40°, at least 45°, at least 50° or at least 55°.

A hinged region 45a, 45b is provided at the junction between each arm and the proximal edge of the adapter, to enable deflection of each arm in a distal direction. The hinged region may be provided, for example, by a localised thinning of the material.

Each deflectable arm 44a, 44b, includes a most-proximally placed surface in the form of a ramped surface 46a, 46b.

Each deflectable arm 44a, 44b also includes a locking face 48a, 48b that is positioned at the free end of each arm, and which is substantially parallel to the longitudinal axis X of the adapter. Each locking face 48a, 48b extends in a distally direction from a junction with a respective ramped surface 46a, 46b.

Each deflectable arm 44a, 44b is configured to mate with a corresponding feature on the nozzle of the enteral fluid source in order to lock the adapter on the nozzle, and prevent inadvertent unscrewing. Examples of corresponding features are shown in FIGS. 1E and 1F and may be in the form of parts of an anti-tamper mechanism. An example of an anti-tamper mechanism is an anti-tamper ring 50, which includes a collar 52 from which spaced-apart protrusions 54a, 54b extend in a distal direction.

Each spaced-apart protrusion 54a, 54b includes a contact point 56a, 56b and a locking face 58a, 58b.

Each contact point 56a, 56b is the point at which contact is made between the ramped surface 46a, 46b of each deflectable arm 44a, 44b, and the corresponding feature 54a, 54b on the anti-tamper ring 50 as the adapter is screwed in a clockwise direction onto the nozzle.

With reference to FIG. 1F, as the adapter is continued to be screwed onto the nozzle, each contact point 56a, 56b is caused to ride along the ramped surface towards the free end of each arm. The downward force applied by via the contact point 56a, 56b of each corresponding feature against the ramped surface 46a, 46b of each deflectable arm as the contact point rides along the ramped surface causes the gradual deflection of each arm in the distal direction.

With reference to FIG. 1G, when each deflectable arm 44a, 44b has been screwed past the respective contact point 56a, 56b on the spaced-apart protrusion 54a, 54b, the subsequent removal of the applied force enables the deflectable arm to spring back into its original (i.e., non-deflected) position.

In this position the locking face 48a, 48b provided at the free end of each deflectable arm 44a, 44b is bought into contact with a respective locking face 58a, 58b provided on each spaced-apart protrusion 54a, 54b.

The inventive combination of the angle of each deflectable arm relative to the longitudinal axis of the adapter and the locking face provided on each deflectable arm irreversibly locks the adapter onto the nozzle and prevents unscrewing in the anti-clockwise direction. This prevents the users inadvertently unscrewing the nozzle, and consequent failure of the fluid-tight connection, as the removable cap is unscrewed from the distal end of the adapter to enable a fluid connection to be made between the adapter and an enteral feed tube.

Second Exemplary Construction of the Enteral Adapter Assembly

With reference to FIGS. 2A-E, a second construction of an enteral adapter assembly for connecting an enteral fluid source (e.g., an enteral feed bag) to an enteral feed tube is shown which is a variant of the first construction. The adapter assembly 110 includes an adapter 120 and a removable cap 130. The cap is shown as being tethered to the adapter. This is advantageous as it prevents the user misplacing the cap.

The adapter 120 is similar in construction to the adapter 20, differing only in the design of the locking members. The locking members are defined by a pair of diametrically opposed deflectable arms 144a, 144b positioned at the proximal end of the adapter 122. Each arm has a so-called "Shark fin" design.

A pair of generally rectangular cut-outs or flex windows 160a, 160b are formed in the wall of the adapter body. The pair of cut-outs are positioned on diametrically opposed sides of the adapter body. A proximal edge 162a, 162b of each cut-out defines a distal edge 164a, 164b of a respective deflectable arm 144a, 144b. Hence, each arm 144a, 144b extends generally perpendicularly to the longitudinal axis "X" of the adapter and does not have a free end.

Each deflectable arm has a first hinged region 145a, 145b, and a second hinged region 147a, 147b provided at opposing ends of the arm. The hinged region may be provided, for example, by a localised thinning of the material. The provision of the hinged regions enables the distal edge 164a, 164b of the respective deflectable arm 144a, 144b to be flexed or "bowed" in a distal direction into the cut-out 160a, 160b.

Each deflectable arm 144a, 144b, includes a most-proximally placed surface in the form of a ramped surface 146a, 146b.

Each deflectable arm 144a, 144b also includes a locking face 148a, 148b which is substantially parallel to the longitudinal axis X of the adapter. Each locking face 148a, 148b extends in a distally direction from a junction with a respective ramped surface 146a, 146b.

Figure 2A:
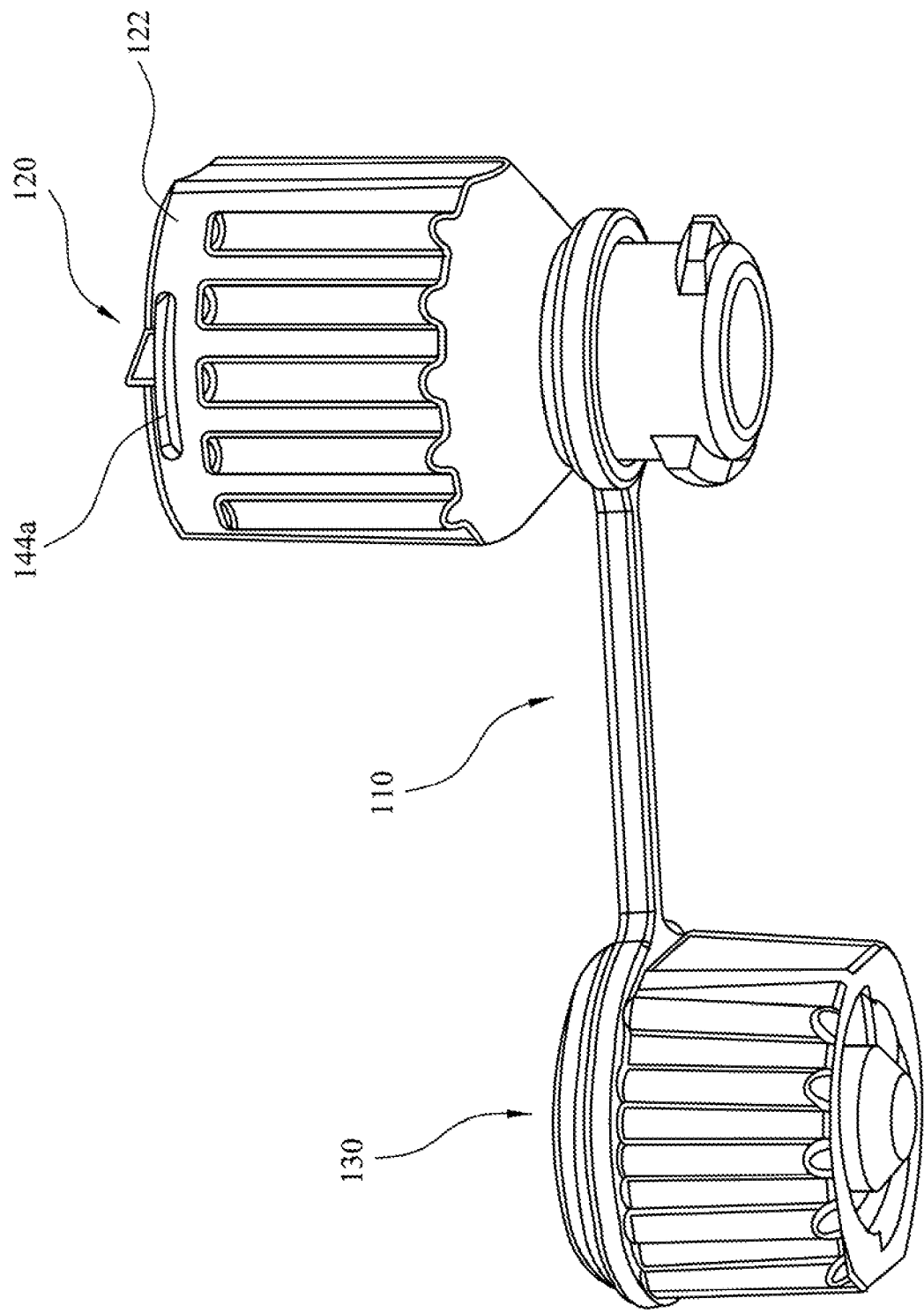
FIG. 2A is a perspective view a second construction of an enteral adapter assembly according to the invention showing the cap tethered to the adapter.
Figure 2B:
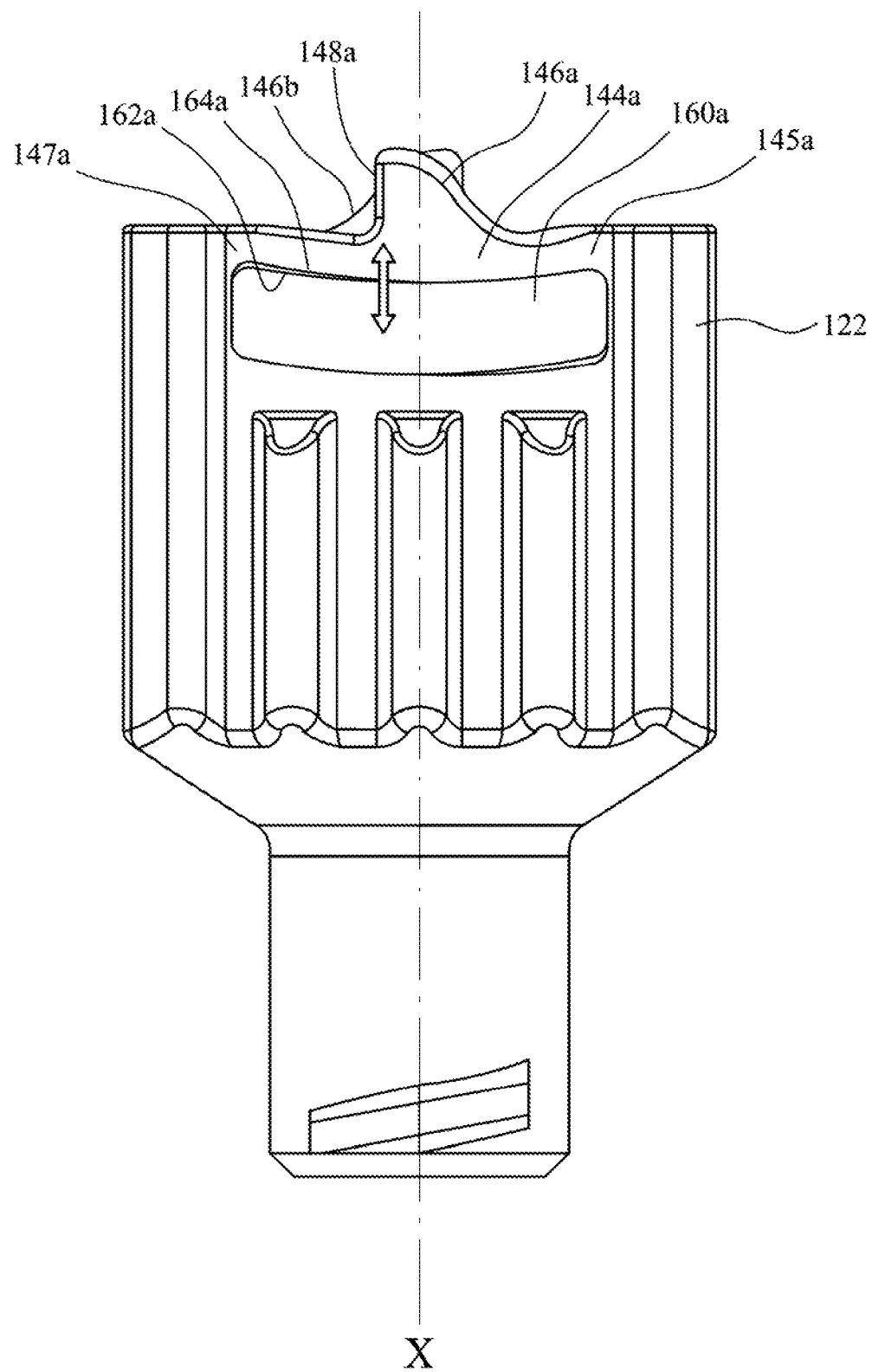
FIG. 2B is a front view of the adapter shown in FIG. 2A.
Figure 2C:
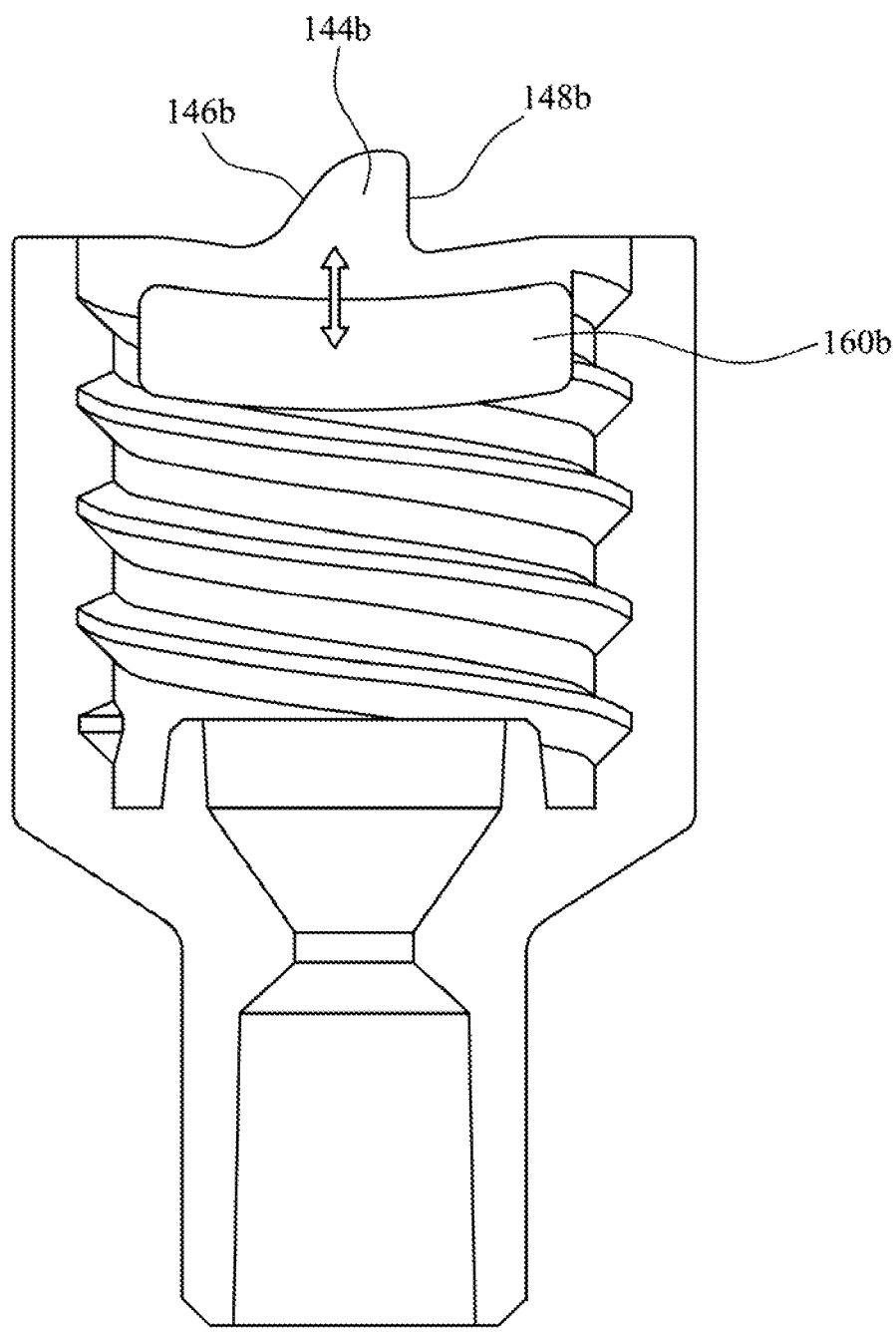
FIG. 2C is a cross-sectional view of the adapter shown in FIG. 2B.
Figure 2D:
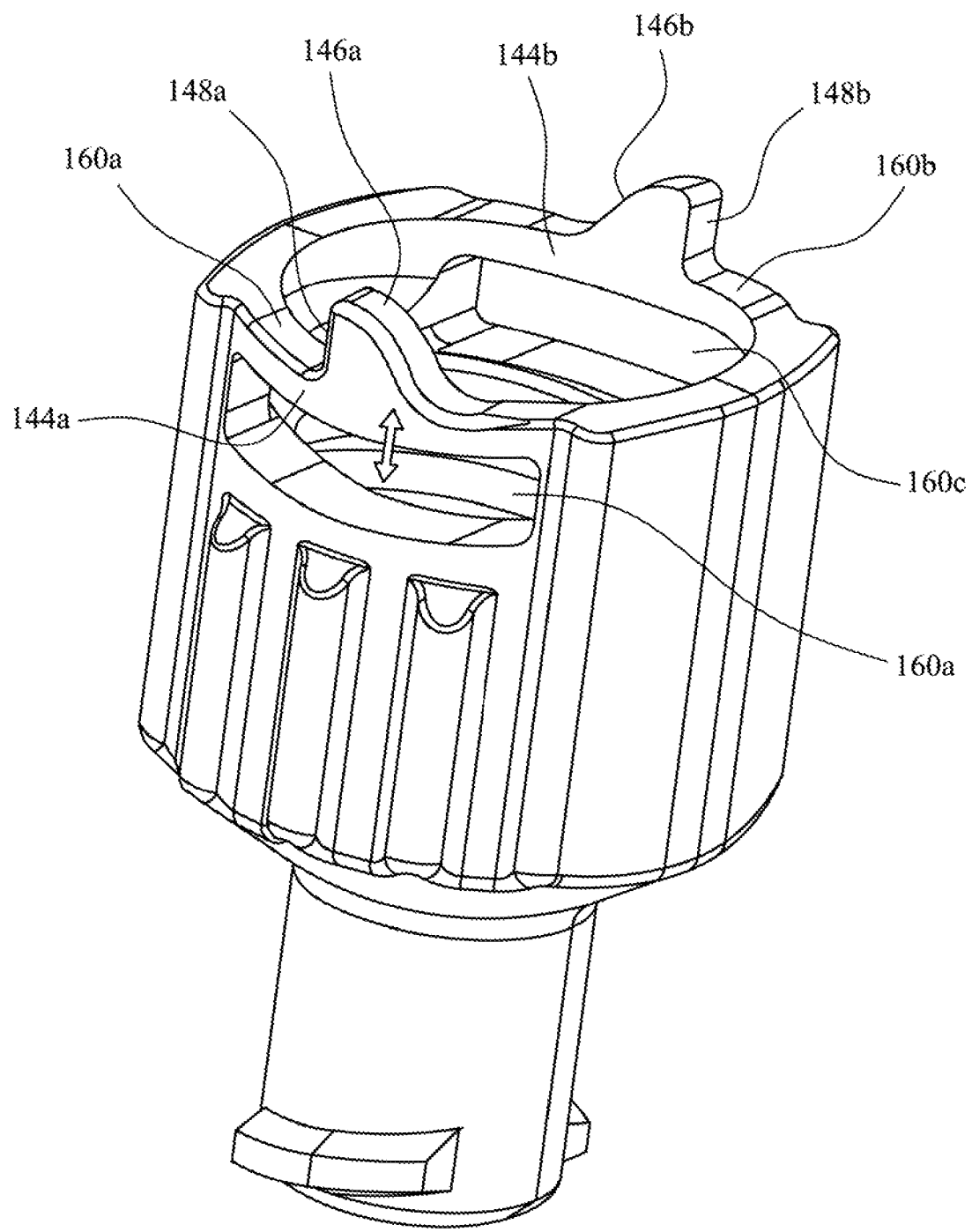
FIG. 2D is an isometric view of the adapter shown in FIG. 2B.
Figure 2E:
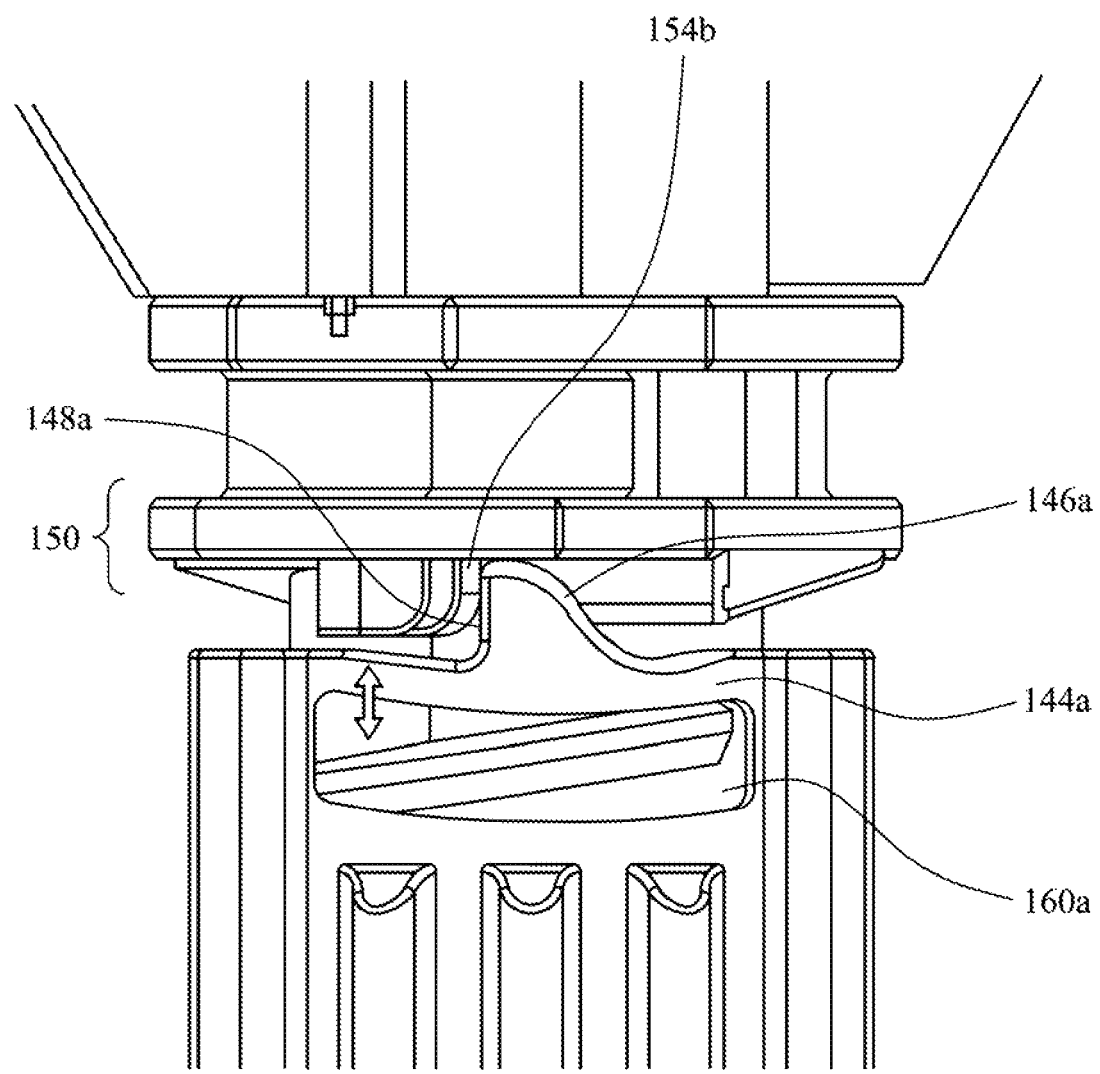
FIG. 2E is a perspective view of the adapter assembly of FIG. 2B engaged with the fluid outlet on the fluid source.

As shown in FIG. 2E, the irreversible locking mechanism between each deflectable arm 114a, 144b and the corresponding feature 154a, 154b on the anti-tamper ring 150 is the same as described above in relation to adapter 10.

Third Exemplary Construction of the Enteral Adapter Assembly

Turning now to FIGS. 3A-3E there is shown a third construction of an enteral adapter assembly for connecting an enteral fluid source (e.g., an enteral feed bag) to an enteral feed tube is shown which is a variant of the first construction. The adapter assembly 210 includes an adapter 220 and a removable cap 230. The cap is shown as being tethered to the adapter. This is advantageous as it prevents the user misplacing the cap.

The adapter 220 is similar in construction to the adapter 20 and adapter 120, differing only in the design of the locking members.

In this construction, the locking members are defined by a pair of diametrically opposed deflectable arms 244a, 244b that are aligned substantially parallel with longitudinal axis of the adapter. The pair of arms define a juxtaposable jaw. This third construction is a so-called "jaw-like" design.

Each deflectable arm has a hinged region 245. The hinged region may be provided, for example, by a localised thinning of the material. The provision of the hinged regions enables a distal portion of each deflectable arm to be flexed outwardly with respect to the longitudinal axis X.

The proximal region of each deflectable arm 244a, 244b includes a ramped surface 246a, 246b that extends at an angle from the proximal end of the adapter in a distally direction and angled away from the longitudinal axis "X".

Each deflectable arm 244a, 244b also includes a locking face 248a, 248b which is substantially perpendicular to the longitudinal axis "X" of the adapter. Each locking face 248a, 248b extends from and a perpendicular to a respective ramped surface 246a, 246b.

Figure 3A:
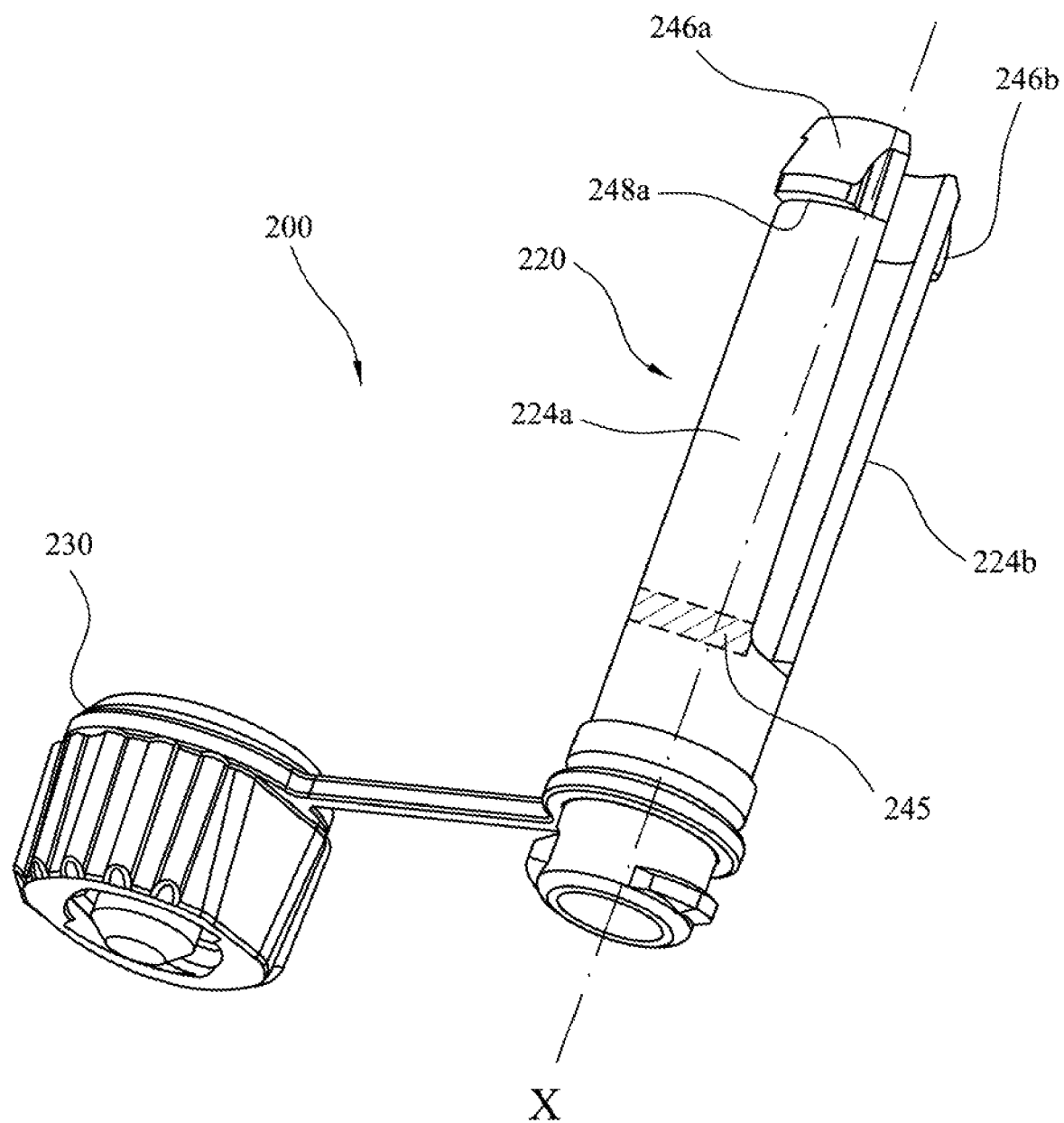
FIG. 3A is a perspective view a third construction of an enteral adapter assembly according to the invention showing the cap tethered to the adapter.
Figure 3B:
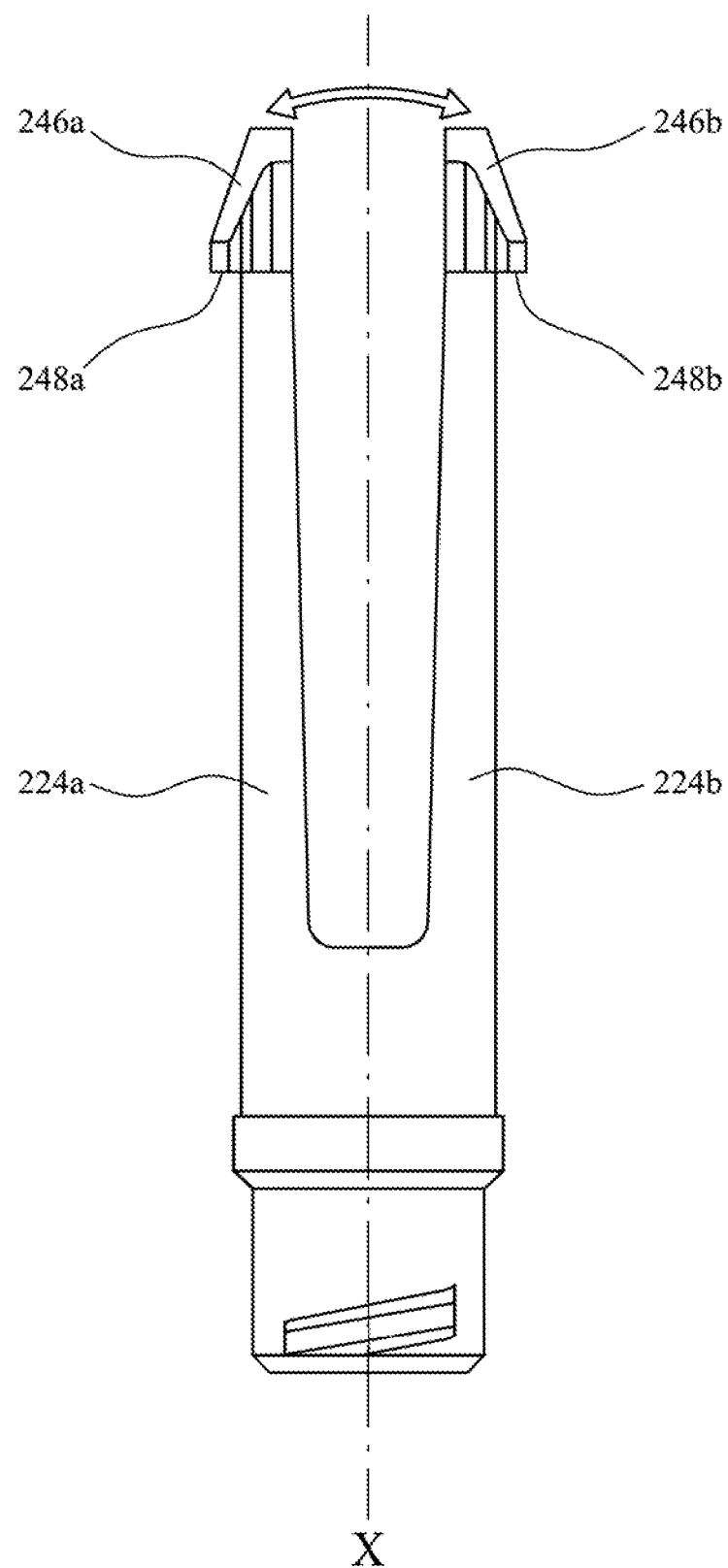
FIG. 3B is a front view the adapter shown in FIG. 3A.
Figure 3C:
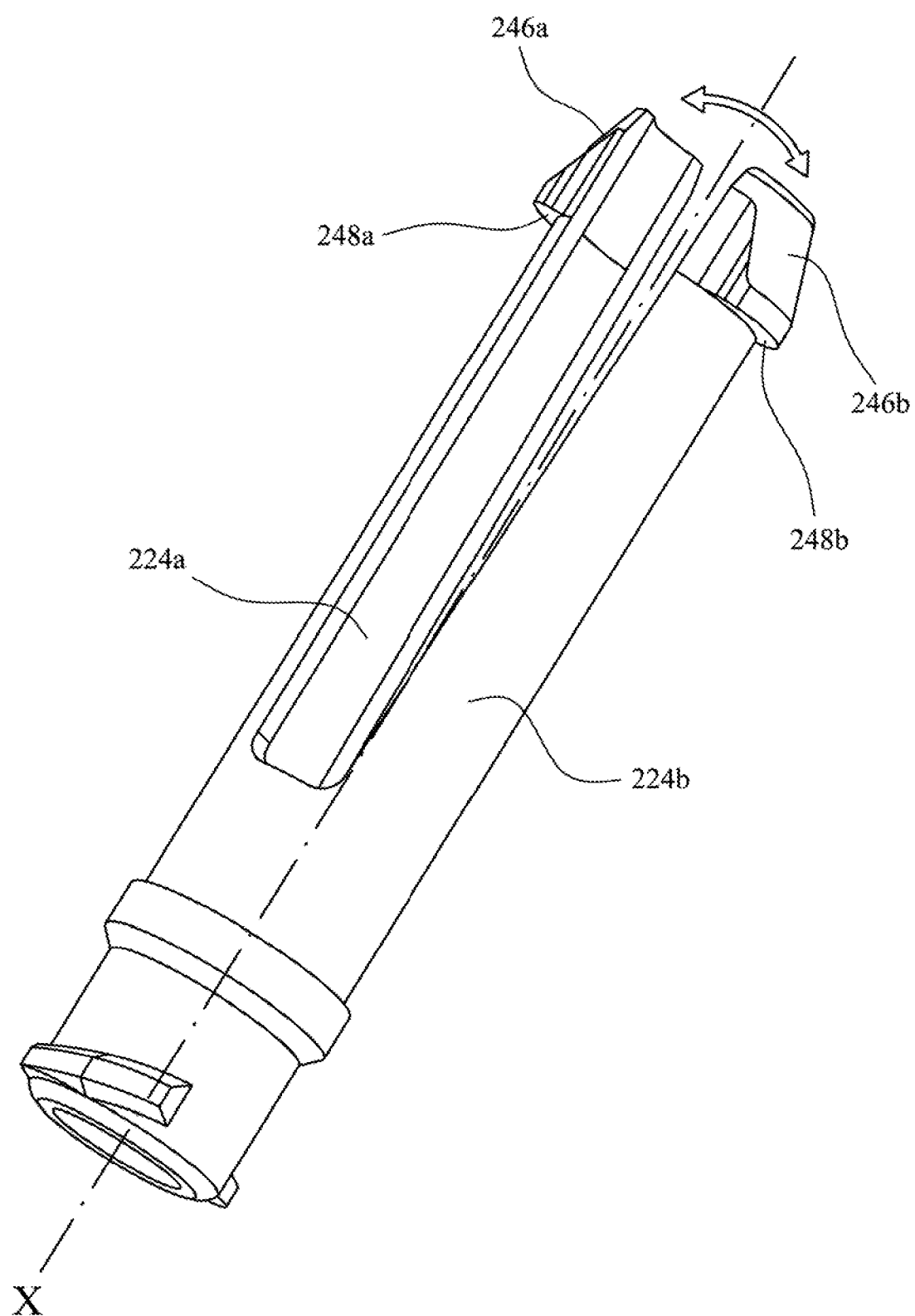
FIG. 3C is an isometric view of the adapter shown in FIG. 3B.
Figure 3D:
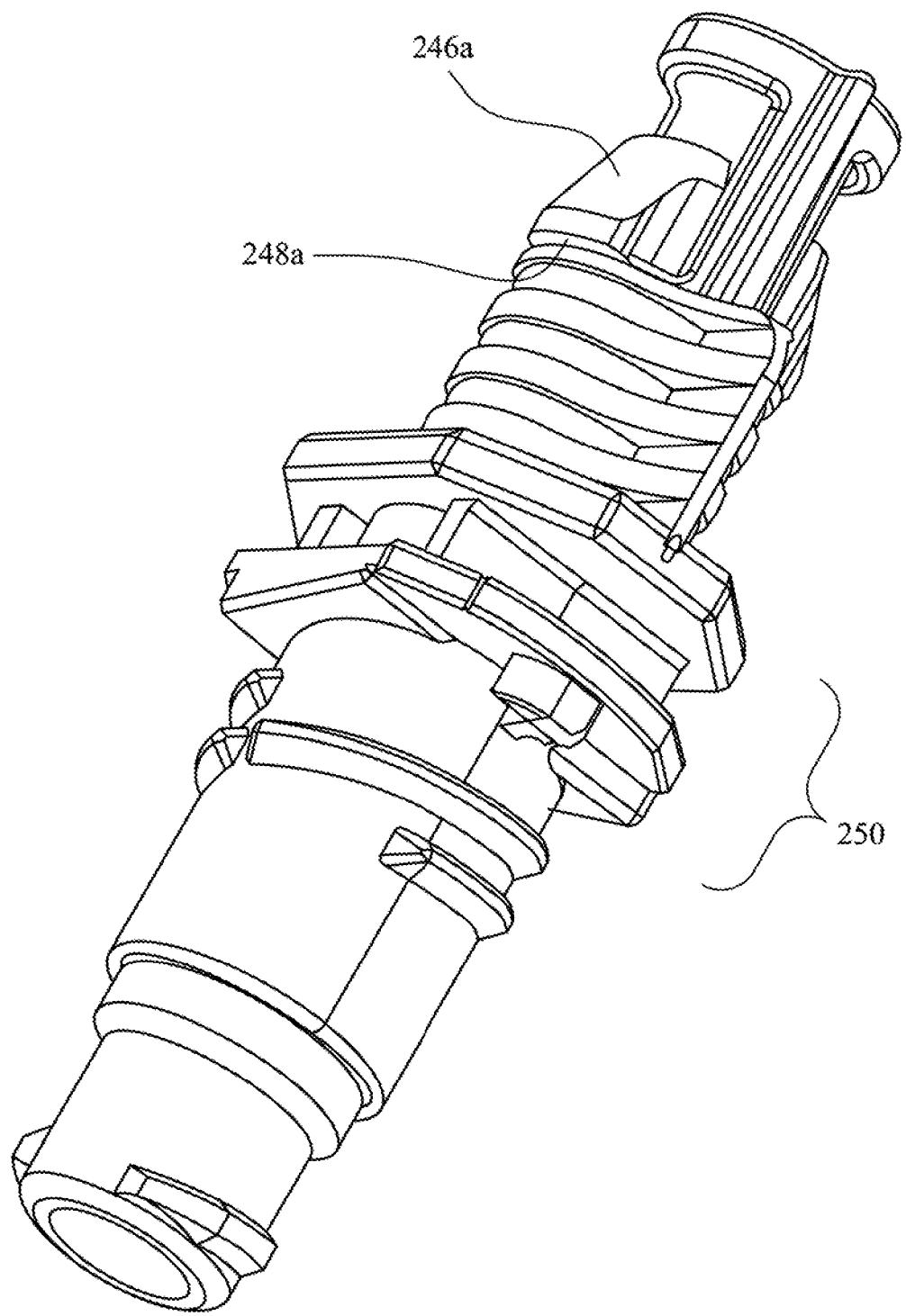
FIG. 3D is a perspective view of the adapter shown in FIG. 3B engaged with the fluid outlet on the fluid source.
Figure 3E:
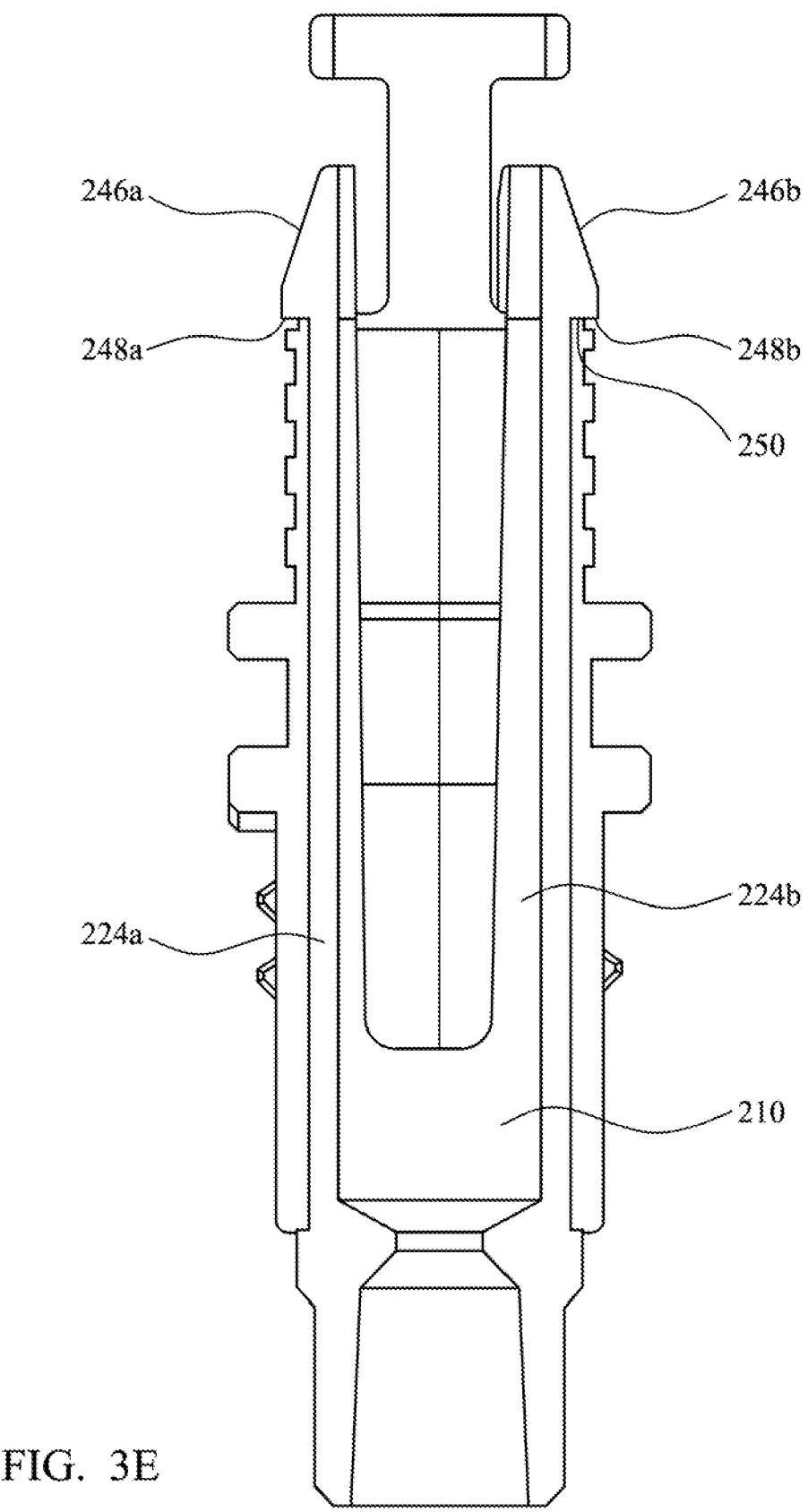
FIG. 3E is a cross-sectional view of the adapter shown in FIG. 3B engaged with the fluid outlet on the fluid source.

As shown in FIGS. 3D and 3E, in use the adapter is inserted up the nozzle of the enteral feed bag. The ramped surfaces 246a, 246b help to guide each respective deflectable arm into the nozzle.

Due to the inner diameter of the nozzle being narrower than the outer diameter of the adapter, the pair of deflectable arms 244a, 244b will be deflected towards each other and be constrained during insertion. When the proximal end of the adapter has exited the nozzle, and the constraining force is removed, each deflectable arm 244a, 244b will deflect back to its original configuration. The locking face 248a, 248b of each deflectable arm will be brought into a locking abutment with a corresponding feature i.e., the proximal rim 250 of the nozzle, to thereby irreversibly lock the adapter to the nozzle.

It will be appreciated by those skilled in the art that changes could be made to the construction described above without departing from the broad inventive concept thereof. It is understood, therefore, that this disclosure is not limited to the particular constructions disclosed, but it is intended to cover modifications within the spirit and scope of the present disclosure as defined by the claims.

The invention claimed is:

1. An enteral adapter assembly comprising:
   an enteral fluid source having a fluid outlet provided with a screw thread;
   an adapter including a proximal end comprising a first connection portion for attaching to the fluid outlet, a distal end comprising a first threaded connection portion for screwing to an end of an enteral feed tube, and a fluid conduit extending between the proximal end of the adapter and the distal end of the adapter, and
   a removable cap having a second threaded connection portion configured for screwing the cap onto the first threaded connection portion,
   wherein the first connection portion of the proximal end of the adapter includes a third threaded connection portion configured for forming a screw connection with the screw thread of the fluid outlet to form a fluid-tight connection between the fluid outlet and the fluid conduit,
   wherein the proximal end of the adapter further comprises a locking member configured to irreversibly mate with a corresponding feature provided on the fluid outlet as the adapter is screwed on to the fluid outlet to prevent removal of the adapter from the fluid outlet and consequent failure of the fluid-tight connection when the cap is unscrewed from the distal end of the adapter,
   wherein the locking member comprises at least one deflectable element that is configured to deflect in a longitudinal direction towards the distal end of the adapter as the adapter is screwed on to the fluid outlet and thereby irreversibly mate with the corresponding feature provided on the fluid outlet.

2. The enteral adapter assembly of claim 1, wherein the corresponding feature provided on the fluid outlet of the enteral fluid source is a part of an anti-tamper mechanism.

3. The enteral adapter assembly of claim 2, wherein the anti-tamper mechanism is a tamper-evident ring.

4. The enteral adapter assembly of claim 1, wherein the at least one deflectable element of the locking member comprises a plurality of deflectable elements spaced apart about the proximal end of the adapter.

5. The enteral adapter assembly of claim 4, wherein the plurality of deflectable elements is circumferentially arranged about the proximal end of the adapter.

6. The enteral adapter assembly of claim 1, wherein the at least one deflectable element of the locking member comprises a first deflectable element and a second deflectable element that are positioned diametrically opposite each other.

7. The enteral adapter assembly of claim 1, wherein the at least one deflectable element comprises a locking face configured to be brought into a locking engagement with a corresponding locking face on the corresponding feature provided on the fluid outlet during attachment of the adapter to the fluid outlet.

8. The enteral adapter assembly of claim 7, wherein the adapter comprises a longitudinal axis extending between the proximal end and the distal end, and wherein the locking face is positioned substantially parallel to the longitudinal axis.

9. The enteral adapter assembly of claim 7, wherein the adapter comprises a longitudinal axis extending between the proximal end and the distal end, and wherein the locking face is positioned substantially perpendicular to the longitudinal axis.

10. The enteral adapter assembly of claim 1, wherein the locking member or the at least one deflectable element is a deflectable arm.

11. The enteral adapter assembly of claim 10, wherein the deflectable arm extends substantially perpendicular to a longitudinal axis.

12. The enteral adapter assembly of claim 10, wherein the deflectable arm extends substantially parallel to a longitudinal axis.

13. The enteral adapter assembly of claim 1, wherein the cap is tethered to the adapter.

14. A kit comprising the enteral adapter assembly according to claim 1 and the enteral feed tube.

15. An enteral adapter assembly for connecting an enteral fluid source with a fluid outlet provided on the enteral fluid source to an enteral feed tube, the assembly comprising:
an adapter including a proximal end comprising a first connection portion for attaching to the fluid outlet provided on the enteral fluid source, a distal end comprising a first threaded connection portion for screwing to an end of the enteral feed tube, and a fluid conduit extending between the proximal end of the adapter and the distal end of the adapter, and
a removable cap having a second threaded connection portion configured for screwing the cap onto the first threaded connection portion,
wherein the first connection portion of the proximal end of the adapter includes a third threaded connection portion configured for forming a screw connection with the fluid outlet to form a fluid-tight connection between the fluid outlet and the fluid conduit,
wherein the proximal end of the adapter further comprises a locking member configured to irreversibly mate with a corresponding feature provided on the fluid outlet provided on the enteral fluid source as the adapter is screwed on to the fluid outlet to prevent removal of the adapter from the fluid outlet when the cap is unscrewed from the distal end of the adapter,
wherein the locking member comprises a deflectable element that is configured to deflect in a longitudinal direction towards the distal end of the adapter as the adapter is screwed on to the fluid outlet and thereby irreversibly mate with the corresponding feature on the fluid outlet.

16. An adapter assembly for connecting a fluid source with a fluid outlet provided on the fluid source to a fluid conduit, the assembly comprising:
an adapter including a proximal end comprising a first connection portion for attaching to the fluid outlet provided on the fluid source, a distal end comprising a first threaded connection portion for screwing to an end of the fluid conduit, and a passage for fluid flow extending between the proximal end of the adapter and the distal end of the adapter, and
a removable cap having a second threaded connection portion configured for screwing the cap onto the first threaded connection portion,
wherein the first connection portion of the proximal end of the adapter includes a third threaded connection portion configured for forming a screw connection with the fluid outlet to form a fluid-tight connection between the fluid outlet and the fluid conduit,
wherein the proximal end of the adapter further comprises a locking member configured to irreversibly mate with a corresponding feature provided on the fluid outlet provided on the fluid source as the adapter is screwed on to the fluid outlet to prevent removal of the adapter from the fluid outlet when the cap is unscrewed from the distal end of the adapter,
wherein the locking member comprises a deflectable element that is configured to deflect in a longitudinal direction towards the distal end of the adapter as the adapter is screwed on to the fluid outlet and thereby irreversibly mate with the corresponding feature on the fluid outlet.

* * * * *